United States Patent [19]

Pieters et al.

[11] 4,194,990

[45] Mar. 25, 1980

[54] CATALYST AND PROCESS FOR THE PRODUCTION OF CHLOROFLUORINATED HYDROCARBONS

[75] Inventors: Wim J. M. Pieters, Morristown; William E. Gates, Green Township, Morris County; Emery J. Carlson, Chatham; John E. Wilkalis, Morris Plains, all of N.J.

[73] Assignee: Allied Chemical Corporation, Morristown, N.J.

[21] Appl. No.: 869,730

[22] Filed: Jan. 16, 1978

Related U.S. Application Data

[62] Division of Ser. No. 767,716, Feb. 11, 1977, Pat. No. 4,088,705.

[51] Int. Cl.$^2$ .................. B01J 27/10; B01J 27/12
[52] U.S. Cl. .................................................. 252/441
[58] Field of Search .................. 260/653.6, 653.7; 252/441

[56] References Cited

U.S. PATENT DOCUMENTS

| 2,024,095 | 12/1935 | Daudt et al. | 260/653.7 |
|---|---|---|---|
| 2,576,823 | 11/1951 | Benning et al. | 260/653.7 |
| 2,578,913 | 12/1951 | Whitman | 260/653.8 |
| 3,183,276 | 5/1965 | Vecchio | 252/441 X |
| 3,379,780 | 4/1968 | Robinson | 260/653.3 |
| 3,398,203 | 8/1968 | Olson | 260/653.7 X |
| 3,476,817 | 11/1969 | Vecchio | 260/653.7 |
| 3,591,646 | 7/1971 | Vecchio et al. | 260/653.6 |
| 3,624,170 | 11/1971 | Wakiyama et al. | 252/441 X |
| 3,644,545 | 2/1972 | Buckman | 252/441 X |
| 4,039,596 | 8/1977 | Pieters et al. | 260/653.7 |
| 4,052,470 | 10/1977 | Nychka et al. | 260/653.8 X |

FOREIGN PATENT DOCUMENTS

| 37-28634 | 11/1962 | Japan | 260/653.8 |
|---|---|---|---|
| 745818 | 3/1956 | United Kingdom | 260/653.8 |

*Primary Examiner*—Patrick Garvin
*Attorney, Agent, or Firm*—Alan M. Doernberg; Jay P. Friedenson; Gerard P. Rooney

[57] ABSTRACT

Catalyst and process for the production of chlorofluorinated hydrocarbons are disclosed by reacting a hydrocarbon with HCl, HF and an oxygen-containing gas under oxychlorofluorination conditions in the presence of a catalytic composition comprising magnesium and copper ions each in combination with fluoride ions and an alkali metal ion, or mixtures thereof, in combination with chloride ions.

9 Claims, No Drawings

CATALYST AND PROCESS FOR THE PRODUCTION OF CHLOROFLUORINATED HYDROCARBONS

This is a division, of application Ser. No. 767,716, filed Feb. 11, 1977, now U.S. Pat. No. 4,088,705.

BACKGROUND OF THE INVENTION

It is known to produce elemental chlorine by the reaction of gaseous hydrogen chloride with elemental oxygen, the so-called Deacon reaction. Moreover, such process can be combined with a process of chlorination wherein gaseous HCl and elemental oxygen are passed in vapor phase in contact with organic material to be chlorinated, under conditions such that the hydrogen chloride is oxidized with production of elemental or nascent chlorine which functions as a chlorinating agent. Such process is known as "oxyhydrochlorination" or "OHC."

The consumption of chlorine in the OHC process promotes oxidation of further quantities of the hydrogen chloride reactant. Representative of the earlier art in this area is an article in the publication, *The Chemical Engineer*, for July-August 1963 at pages 224-232 by J. T. Quant et al. A catalyst is used in such processes, especially copper chloride upon a carrier, usually a silicious carrier. Usually the catalyst is promoted by another metal chloride, especially alkali metal chloride, and/or rare earth metal chloride. For chlorination of alkanes and chloroalkanes, the temperature range employed is broadly from 350° C. to 550° C.; and for alkenes the broad temperature range is 200° C. to 350° C. Ordinarily, the elemental oxygen is supplied as oxygen or air, although the process is operative with more concentrated forms of elemental oxygen. Pressures used are generally about atmospheric, but can be higher, e.g. up to about 10 atmospheres.

In a modification of the "OHC" process just mentioned, fluorination can be effected upon a substance containing CCl groups, susceptible of fluorination by action of hydrogen fluoride. Hydrofluorination of chlorocarbons has been described using several catalyst systems, e.g. chromium oxyfluoride (British Pat. No. 1,025,759), chromium fluoride (U.S. Pat. No. 2,576,823 and British Pat. No. 640,486), iron chloride (British Pat. No. 640,486), thorium fluoride (U.S. Pat. No. 3,183,276), and antimony halides (U.S. Pat. No. 2,024,095). Hydrogen chloride under these reaction conditions may be returned to the oxychlorination process. A variant is to expose a hydrocarbon susceptible of chlorination to gaseous HCl and elemental oxygen under conditions suitable for oxyhydrochlorination; and to include hydrogen fluoride in the vapor phase to react with the chlorinated organic hydrocarbon formed. Such process is known as "oxychlorofluorination" or "OCF."

A representative disclosure of an OCF process is in British Pat. No. 745,818, issued Mar. 7, 1956. In that patent the catalyst is aluminum fluoride impregnated with cupric chloride. Whitman U.S. Pat. No. 2,578,913, issued Dec. 18, 1951, relates to a somewhat similar fluorination process using in most examples a catalyst of copper oxide supported on alumina; and disclosing also (column 5, lines 23-35) use of oxides or salts of metals such as copper, lead, chromium, and iron group metals supported on alumina, calcium fluoride, or copper gauze; also copper chromite. Also of interest is U.S. Pat. No. 3,476,817, issued Nov. 4, 1969, which discloses a chlorofluorination reaction in which a hydrocarbon is reacted with chlorine in the presence of HF, a Deacon type catalyst and oxygen in an amount sufficient to improve the catalyst life. Other patents of interest include U.S. Pat. Nos. 3,379,780 and 3,398,203.

Problems which have been encountered in employing either the "OHC" or "OCF" process commercially arise from the fact that the copper chloride, has enough vapor pressure at the required temperatures so that it migrates by sublimation. If in order to reduce the temperature required for reaction, the copper chloride is admixed with promoter salts such as potassium chloride, lithium chloride, rare earth metal chlorides and the like, eutectic compositions are formed which melt at the reaction temperatures generally required for these processes and tend to coalesce. Consequently the known catalysts for OHC and OCF reactions show markedly decreasing catalytic effectiveness with continuing use.

Attempts have been made to minimize these problems by obtaining more active catalysts, which would operate at lower temperatures than usually required; or by obtaining the copper catalyst in a stabilized active form, sufficiently stable at the reaction temperatures to avoid sublimation and melting during use. These prior efforts have not been sufficiently successful, so far as we are aware, to allow the general commercialization of such processes under existing ecomonic conditions.

An additional aspect significant from a commercial standpoint is the reactivity of the promoted copper chloride catalysts towards the materials of construction which would normally be considered for use under OHC and OCF reaction conditions. Inconel 600, a material of construction one would consider for such use, was found to be attacked by the metal halide component of the catalyst at 400° C. at a corrosion rate of about 6 inches per year - a corrosion rate obviously unacceptable from a commerical standpoint.

SUMMARY OF THE INVENTION

The present invention is directed to new catalysts and to chlorination-fluorination (OCF) reactions of organic compounds using such catalysts. The catalysts of the present invention consist essentially of a catalytic is a catalytic composition of at least about 60% by weight of said composition of magnesium and copper ions each in combination with fluoride ions, and an alkali metal ion or mixtures thereof in combination with chloride ion. Suitable alkali metal ions include sodium, potassium and lithium. Of particular interest as an oxychlorofluorination catalyst is a catalytic composition comprising in combination magnesium fluoride, copper fluoride, potassium chloride and lithium chloride. These catalytic compositions were determined to have corrosion rates under OCF conditions on Inconel 600 of about 20 to 30 mils per year.

In the oxychlorofluorination reaction, the oxidation of HCl, chlorination of the hydrocarbon and fluorination of the chlorohydrocarbon can all take place in a single reaction vessel. The chlorination reaction replaces one or more available hydrogen atoms in the starting organic material with chlorine to give a chlorinated product and HCl. In the presence of a suitable Deacon-type catalyst the HCl is oxidized back to chlorine which then is available for further chlorination. In the presence of a fluorination catalyst, the chlorinated products are fluorinated by HF to yield chlorofluorinated products. In the present process it is preferred to form from methane $CCl_3F$ and $CCl_2F_2$ in high conversion and high selectivity. Depending on the conditions chosen, the final products are more or less partially fluorinated and may or may not contain hydrogen.

The hydrocarbon starting materials which may be used for the oxychlorofluorination reaction may be any saturated or ethylenically unsaturated material with CH groups susceptible to chlorination. Preferred materials because of the commercial significance of the end products are acyclic hydrocarbons containing up to four carbon atoms. Such preferred class of materials includes such compounds as methane, ethane, propane, butane, ethylene, propylene, butylene, isobutylene and butadiene. The preferred saturated acyclic hydrocarbons are methane and ethane. The preferred unsaturated acyclic hydrocarbons are ethylene and isobutylene.

The hydrohalocarbon class of starting materials in which the halo atoms are selected from fluorine and chlorine may also be saturated or ethylenically unsaturated. These materials must contain at least one hydrogen atom. The halo atoms may be all chloro, all fluoro, or both. Preferably, these starting materials contain more atoms of hydrogen than halogen. Still preferably, the number of flourine atoms in the molecules does not exceed more than one for each carbon atom present. Illustrative starting materials of this class include methyl chloride, methyl fluoride, monochlorodifluoromethane, methylene chloride, methylene fluoride, chloroform, ethyl chloride, ethylene chloride, ethylene fluoride, ethylene dichloride, ethylene difluoride, trichloroethane, vinylidene chloride, vinyl chloride, trichloroethylene, and the monochloro, dichloro and trichloropropanes, butanes, butylenes and butadienes. The preferred aliphatic hydrohalocarbon starting materials are methyl chloride and ethyl chloride.

Oxygen or oxygen-containing gas refers to oxygen or an oxygen-containing mixture with gases which are not reactive under the process conditions employed. Examples of suitable oxygen-containing gases include elemental oxygen, oxygen enriched air, air, air mixed with inert gases and mixtures of oxygen, air and inert gases; elemental oxygen is especially preferred. The theoretical quantity of oxygen in an oxygen-containing gas required for the oxychlorination reaction is the stoichiometric amount required to convert C-H bonds to C-Cl bonds in accordance with the following formula:

In other words, 0.50 mole oxygen for each C—H bond in the starting material is required. A 50% deficiency may be employed with satisfactory results, or at least 0.25 mole oxygen for each C—H bond in the starting material. Generally, it is preferred to employ up to about a 50% excess, or 0.75 mole oxygen for each C—H bond in the starting material. Large excesses of oxygen will not deleteriously affect the reaction, except for the possibility of creating a flammability problem.

Elemental chlorine, HCl or mixtures thereof may be used during the chlorination reaction. Presently, HCl for economic reasons is the preferred chlorine source for the oxychlorofluorination reaction. HCl may be supplied from an outside source or, it may be prepared in situ, by the reaction of the HF feed with a chlorine-containing hydrohalocarbon starting material if present. The quantity of HCl used in the reaction should be the stoichiometric amount required for hydrogen replacement and/or saturation of ethylenically unsaturated bonds in the starting material. The theoretical amount required is 1 mole of HCl or equivalent of $Cl_2$ (0.5 mole) for each C—H bond and C=C bond present in the starting material. A 50% deficiency of HCl or equivalent of $Cl_2$, or 0.50 mole HCl or equivalent of $Cl_2$, for each C—H bond and C=C bond present in the starting material, may be employed with good results, particularly if it is desired to favor the production of lower chlorinated products. Excess HCl or $Cl_2$ may be used to insure maximum conversions of the highly chlorinated products without deleterious effects. If it is desired to preserve some C—H bonds in the final product, a somewhat greater deficiency of HCl should be employed, but in no event less than 2.0 moles of HCl for each mole of starting material. Elemental chlorine may be used in addition to or in place of the HCl. In the case that HCl is charged, such would be converted to chlorine by the Deacon reaction and chlorine would then be the active chlorinating agent.

The quantity of HF to be employed is equal to at least one mole of hydrogen fluoride per mole of organic starting material for every fluorine atom desired in the end product which is to be achieved by the fluorination reaction. It is feasible in the oxychlorofluorination environment to produce the desired fluorinated products with substantial conversion of HF. It is preferred that substantially all of the HF be utilized during the fluorination reaction. In the case of methane starting material, for example, the preferred molar ratio of HF to methane is about 1–2.5:1.

The catalysts of this invention may be prepared by one of the following methods: fusion, precipitation or impregnation techniques. These will be described in more detail hereinbelow. Referring now more particularly to a method of preparation of our catalysts, the catalyst can be prepared from oxides or hydroxides of magnesium and copper precipitated, together, from an aqueous solution, incorporating a source of alkali metal, especially sodium, potassium and lithium ions; then exposing the composition at elevated temperatures to hydrogen fluoride.

Alternatively and preferably, our catalyst can be prepared by precipitating, together, magnesium fluoride and copper fluoride from aqueous solution, incorporating a source of the alkali metal and heating this product and recovering the final catalyst composition.

Catalysts can be obtained by precipitating, together, magnesium and copper fluorides from an aqueous solution of salts thereof such as chlorides, filtering the precipitate and by combining the resulting precipitate with an aqueous solution of potassium fluoride at room temperature; drying the precipitate; heating the product for several hours at temperature of at least about 400° C. but not above about 700° C.; and washing with organic solvent to remove thermally unstable copper-containing material, e.g. copper chlorides and copper oxides.

The required coprecipitation is advisably accomplished by maintaining excess fluoride present, as by adding aqueous solution of magnesium and copper chlorides to excess aqueous potassium fluoride solution.

Suitable organic solvents for washing the heat-treated coprecipitate include acetonitrile (solvent of cuprous chloride) and methanol (solvent of cupric chloride). Slight acidification (HCl) of the acetonitrile is desirable to increase uptake of cuprous chloride therein.

Oxychlorofluorination reaction temperatures are elevated and may vary depending on the starting material chosen, the catalyst and other factors. Generally, reaction temperatures should be maintained between about 300°–600° C., preferably between about 350°–550° C. and, still preferably, between about 380°–500° C. If the reaction temperature is excessive in a particular environment, then the combustion of the hydrocarbons or halohydrocarbons or the hydrolysis of the halohydrocarbons may become excessive. If the reaction temperature is unduly low there will be a decline in the rate of the oxidation of HCl. The ideal reaction temperature for a particular oxychlorofluorination environment will depend on the starting materials chosen, the catalyst and other factors, as can readily be determined by those skilled in the art assisted by the considerations discussed above.

Contact or residence time may be up to about 20 seconds. If contact times substantially above 20 seconds are employed, substantial losses to combustion and to hydrolysis occur and the production capacity per unit volume of catalyst decreases. If the contact times are too low, satisfactory conversion rates cannot be obtained. Accordingly, contact times should be maintained between about 0.1 to 10 seconds, preferably between about 0.05–5 seconds. For fixed bed operation, the preferred contact time is from about 1–10 seconds and, still preferably, from about 0.5–5 seconds. By "contact" or "residence" time (C.T. or R.T.) is intended to mean essentially the time that the feed materials contact each other in the presence of the catalyst, or, more precisely in the case of a fixed bed design(X):

$$C.T.X. \text{ (seconds)} = \frac{\text{Catalyst Volume (ml)} \times 273° \text{ K.} \times 3600 \text{ sec/hr} \times \text{pressure (atm)}}{22{,}400 \text{ ml} \times \text{reactor temperature (°K.)} \times \text{moles (reactants)/hr.}}$$

Pressure is not a critical consideration as the reactions described herein may be conducted uner atmospheric pressure or superatmospheric pressures. In the preferred embodiment, atmospheric pressure is employed, but pressures up to about 200 psig may be utilized.

The chlorination, fluorination and Deacon reactions are highly exothermic. It is desirable to control the exothermic heat of such reaction to avoid pyrolysis, carbonization, combustion and other undesirable side reactions.

Mechanical cooling means may be employed to control the exotherm, such as cooling jackets, cooling spray, cooling coils or other suitable heat exchange means. Another way to control the exotherm is by diluting the catalyst with an inert, solid material, such as calcium fluoride.

Another way to control the exotherm is by adding an inert gas to the reaction gas stream. By "inert gas" is intended to mean a diluent gas which is inert to reaction with the organic reactants and with chlorine, oxygen, water or HCl, but not necessarily inert to reaction with hydrogen fluoride. $CO_2$ would be a suitable inert diluent. The amount of diluent to be used is that which is needed to control the reaction temperature of the particular reaction involved. This will depend on the amount of chlorination taking place and the nature of the diluent used. The preferred amount of diluent may be readily determined by those skilled in the art. Generally, the molar ratio of the diluent to the carbon containing feed materials ranges from about 0.5–4:1, with the preferred ratio ranging from about 1–2:1. At the end of the reaction, the diluent may either be recycled or discarded.

The preferred way to control the exotherm is by recycling one or more halogenated hydrocarbons from the product mixture to the reaction mixture. The recycled halogenated hydrocarbons may be partially chlorinated reaction products, completely chlorinated reaction products and/or underfluorinated reaction products. The recycled halogenated hydrocarbons may be inert to further reaction or they may be subject to further reaction. In the case of methane, for example, the recycled halogenated hydrocarbon may be a single substance such as $CCl_4$ or $CFCl_3$, or a mixture of same and underchlorinated and other underfluorinated methanes. In the case of ethane, for example, the recycle can be a single compound such as $C_2Cl_4$ or $C_2Cl_3F_3$, or a mixture of the same with underchlorinated and other underfluorinated ethanes. If a recycle medium is employed, about 1–6:1 molar ratio of recycled halogenated hydrocarbon to hydrocarbon starting material should be employed, with a preferred molar ratio of about 2–4:1. There is nothing critical about the upper limit for the concentration of the recycled products, except from the standpoint of unit capacity and economy.

In addition to the advantage of providing control over reaction exotherm, use of a recycle affords the advantages of higher utilization of HF, attainment of higher yields of the more desired fluorinated products, a more efficient use of oxygen, less combustion, higher conversion of reactants and a means of control over final product distribution. A high HF utilization is particularly important since recovery of substantial amounts of unreacted HF for recycling is expensive and adds substantially to manufacturing costs. Recycle with underfluorinated products results in further fluorination of the underfluorinated recycle material and thus provides control over the desired product distribution in the final product mix.

Simple experimentation with the make-up and quantity of the recycle in a particular environment will permit ready determination of optimum HF utilization conditions and optimum conditions for achieving the product distribution desired. The advantageous use of recycle in a chlorofluorination reaction is disclosed in U.S. Pat. No. 3,442,962. The environment of the present invention is significantly different from that of U.S. Pat. No. 3,442,962, however, in that the invention environment contains a significant amount of oxygen and water which is a by-product of the Deacon reaction. The literature would suggest that acyclic hydrocarbons and chlorinated acyclic hydrocarbons would be grossly decomposed by the oxidative and hydrolytic environment of this invention. (*Oxidation and Hydrolysis of $CH_4$*, Encyclopedia of Chemical Reactions, C. A. Jacobsen, Vol. II, Entries 1124, 1125, 1130, 1140, 1141, 1143, 1161; *Oxidation and Hydrolysis of $CCl_4$*, Organic Chlorine Compounds, E. H. Huntress, p. 578; *Oxidation and Hydrolysis of $CHCl_3$*, Organic Chlorine Compounds, E. H. Huntress, pp. 550–551.) Contrary to this expectation, under the conditions described herein, the loss of acyclic hydrocarbon starting materials, such as methane, and chlorinated acyclic hydrocarbons to combustion and hydrolysis is very minor.

Any combination of the above-described means of temperature control may be employed.

The process of the invention is carried out by passing the gaseous reactants through a bed of the catalyst material in finely divided or granular solid form. The catalyst bed may be operated as a fixed bed, that is to say by keeping the gas velocity low enough that the bed of solid catalyst particles remains essentially static. The catalyst bed may also be operated as a dynamic bed. By increasing the gas velocity of the reactants some of the catalyst particles become dynamically suspended in the reactant gas stream. The height of the catalyst bed therefore expands. Such beds are generally referred to as "dynamic beds". As is known in the art, if the gas velocity is increased still further, all the catalyst bed particles become suspended and ultimately the bed may assume a highly turbulent condition known and referred to as a fluidized bed. Exact conditions required to establish a fluidized bed condition depend on the particle size of the catalyst composition, the gas velocity, the density of the particles and other factors.

Preferably the process of the invention is carried out in a continuous manner using a reactor comprising a plurality of vertical tubes which are charged with the supported catalytic material in finely divided or granular form. The hydrocarbon starting material, the oxygen-containing gas, the chlorinating agent and hydrogen fluoride may be metered into the bottom of the reactor tubes through calibrated flowmeters. Prior to entry into the bottom of the reactor tubes the reactants are pre-heated to approximatey the reaction temperature desired. Separate feed lines should be used for materials which would othewise prematurely react before passage to the reactor tubes. For example, methane and chlorine will react thermally if present in the same heated lines, as will HF and $CCl_4$. Accordingly, these materials should be fed through separate lines. In accordance with the description herein, optional additional feed streams may be fed into the bottom of the reactor, such as a halogenated hydrocarbon recycle stream, and an inert diluent stream. Liquid reactants may be metered from calibrated reservoirs through pumps.

At the inlets to the fixed catalyst bed, relatively short hot zones will develop. These zones are generally 50°–100° C. higher in temperature than the reactor temperatures. Such temperature gradients are tolerable. However, if excessive temperatures are generated in the hot zones, undesirable combustion and carbonization reactions could result. In such an event, the temperatures of such hot zones should be controlled by employing any of the methods discussed herein for exotherm control.

Pressures, temperatures, contact times and flow rates of reactants are regulated to produce the desired product composition with optimum yields and utilizations of reactants in accordance with the discussion herein. Reaction products are continuously removed from the top of the reactor tubes.

Recovery and purification of the desired products, by-products and unreacted reactants, may be accomplished by conventional means such as distillation procedures normally conducted at elevated pressures. For example, in the case of the oxychlorofluorination of methane, catalyst particles carried over in the exiting product gases may be separated by cyclones for return to the reactor. The product gases may then be cooled and partially condensed. Condensed aqueous HCl and HF are phase-separated from condensed organics, and may be recycled to the reactor after partial or complete dehydration. Condensed organics may be revaporized for further purification, or treated as a liquid phase. Organic vapors are neutralized by contacting with dilute caustic in a scrubber. The organic vapors may then be dried by contacting with concentrated sulfuric acid. The dried neutralized organic vapors are then compressed and fed to a distillation unit (still) to separate low boiling components, such as $CO_2$, oxygen, $CH_4$, $CClF_3$ and other trace low boilers, from higher boiling components such as $CCl_4$, $CCl_3F$, $CCl_2F_2$, $CHCl_3$, $CH_2Cl_2$ and other materials. A series of continuous distillations is used to separate the higher boiling materials into products, such as $CCl_3F$, $CCl_2F_2$, and chlorinated or partially chlorinated intermediates, such as $CCl_4$, $CHCl_3$, $CH_2Cl_2$, and other trace materials. The products may be further purified, if desired, by recycling to the reactor, depending on the product distribution desired.

A variety of modifications and variations of product recovery and purification may be employed by persons skilled in the art and will depend on the nature of the feed materials and product mixes obtained. Such procedures are well within the skill of the art and do not form a part of this invention.

Materials of construction for the reactor and associated equipment should be resistant to the reactants of the oxychlorofluorination process in the environment employed.

The following examples illustrate practice of the preferred embodiments of the present invention in preparing the catalyst and the use of such catalyst in the oxychlorofluorination of methane. The advantages of the present invention will be apparent therefrom. In the examples, the stated reactant feed rates were measured at 25° C., atmospheric pressure, temperatures refer to degrees Centigrade, and the following terms which may be used hereinbelow, unless otherwise specified, have the meanings given below. All quantities of materials referred to are in moles and all percentages given are on a weight basis, except for the terms defined below or unless otherwise specified.

The headings of the table are explained as follows, wherein [ ] represents mole concentration per 100 moles of the inlet reactants (i.e., $CH_4$, $O_2$, HF and HCl) and [CM] represents total moles of net products ($CH_3Cl + CH_2Cl_2 + CHCl_3 + CCl_4 + CCl_3F + CCl_2F_2$).

(1) Residence time: (catalyst void space)/(inlet gas flow at reaction temperature)

(2) $CH_4$ conversion: $100\{[CH_4]in — [CH_4]out\}/[CH_4]in$ (3) HF conversion: $100 \times \{[HF]in — [HF]out\}/[HF]in$ (4) $CH_4$ selectivity: $100\{[CM]/[CH_4]in — [CH_4]out\}$ (5) HF selectivity: $100 \times \{2[CCl_2F_2]net + [CCl_3F]net\}/\{[HF]in — [HF]out\}$, where "net" indicates [ ]out — [ ]in.

(6) Yield: $100[CM]/[CH_4]in = 100 \times \{[CH_3Cl]net + [CCl_4]net + [CH_2Cl_2]net + [CHCl_3]net + [CCl_3F]net + [CCl_2F_2]net\}/[CH_4]in.$ (7) Overall reaction rate: Reactant flow in moles per sec. $\times \{[CH_4]in — [CH_4]out\}/100 \times$ gms. of catalyst in the tube (8) Specific reaction rate: Overall reaction rate/Catalyst surface area in sq. meters per gm.

(9) Extent of "Deacon" reaction: $100 \times \{[HCl]in + [HCl]formed — [HCl]out\}/\{[HCl]in + [HCl]formed\}$, where $[HCl]formed = \{1[CH_3Cl]net + 2[CH_2Cl_2]net + 3[CHCl_3]net + 4[CCl_4]net + 5[CCl_3F]net + 6[CCl_2F_2]net\}.$

(10) "performance Factor" rates the performance in terms of HF conversion, overall HCl utilization, selective conversion of methane and product distribution of $CCl_3F$ with respect to $CCl_2F_2$, calculated as follows:

Performance Factor =

$$\frac{\left[2 \times \left(\frac{A}{90}\right)^3 \times \left(\frac{C}{90}\right)^3 \times \left(\frac{D}{80}\right) \times 100\right] + \text{Product Distribution}}{3}$$

wherein:

$$A = \frac{CCl_3F(\text{net}) + 2\ CCl_2F_2(\text{out})}{HF(\text{in}) - HF(\text{out})} \times 100;$$

$$B = HCl(\text{in}) + 6\ CCl_2F_2(\text{out}) + 5\ CCl_3F(\text{net}) + \\ 4\ CCl_4(\text{net}) + 3\ CHCl_3(\text{net}) + \\ 2\ CH_2Cl_2(\text{net}) + CH_3Cl(\text{net}) + \\ 2\ COCl_2(\text{out}) + 2\ Cl_2(\text{net})$$

$$C = \frac{B - HCl\ (\text{out})}{B} \times 100$$

$$D = \frac{CCl_4(\text{net}) + CFCl_3(\text{net}) + CCl_2F_2(\text{out})}{CH_4(\text{in}) - CH_4(\text{out})} \times 100$$

and Product Distribution = Absolute Value of $$\left[\sin\left(\frac{90° \times CF_2Cl_2(\text{out})}{CFCl_3(\text{out})}\right)\right] \times 100$$

(11) The "Sum of Errors" indicates how closely the analysis of reactants and products approached to material balance. The procedure for determining these "Errors" is as follows:

Material balance for the chemical in the system is estimated by computer, using a linear programming technique. Stoichiometry is impressed by supplying a set of balanced chemical equations to the program which can account for all reactants and final products of the OCF program. One function of the program is to select the extent of each (including zero) that could account for successively "less costly" estimates of the material balance, finally of the least costly. The program assigns linear program "costs", in this case incremental penalties (results of which are to be summed and minimized) for adjusting the chromatographically determined reactant and product concentrations. Costs are assigned on the basis that those associated with most precisely analyzed compounds be high, those with less precisely analyzed compounds be low.

In the Examples conducted the "least cost" material balance resulting from the catalyst run (at a given set of conditions) is printed. The values for each inlet component are normalized to give 100 moles total. The exit components are on the same scale. The sum of costs (i.e., the product of assigned cost × change in each concentration), resulting upon adjusting the experimental concentration values to arrive at the "least cost" material balance, is printed as SUM OF ERRORS.

The following are Examples illustrating the preparation of the preferred catalyst and its use in the oxychlorofluorination of methane.

EXAMPLE I

A solution was prepared by dissolving 14.6 g $CuCl_2$ and 88.1 g $MgCl_2\ 6H_2O$ in 200 ml of deionized water. A second solution was prepared by dissolving 94.1 g KF in 300 ml of deionized water. These solutions were combined by adding the second solution to the first with stirring. Cu and Mg were present in a nominal ratio of 1 to 4 atoms. KF was in excess. A precipitate of fluoride salts was formed. The mixture was allowed to stand for several hours. The mixture was reslurried in about 3 liters of water, heated to 80° C., allowed to cool and stand for 16 hours. The mixture was placed on a large filter funnel and filtered. The solids were collected, dried at 150° C., and finally calcined at 400° C. for 16 hours. 45.3 g of solid material were recovered.

Separately a mixture of 5.5 g KCl and 4.5 g LiCl was blended together and then fused (melted) by heating in a test tube under a blanket of nitrogen (to exclude air and moisture). After cooling, under nitrogen, the solidified melt was ground to a mesh size through 20 mesh in a dry box under nitrogen. The mole ratio of KCl to LiCl was 41 to 59.

Then 22.7 g of the copper-magnesium fluoride composition and 6.0 g of the potassium lithium chloride composition were blended under nitrogen, placed in a test tube, and carefully heated with a gas burner while turning and stirring to melt the chloride salt phase and disperse it into the support phase. This was carried out under a stream of nitrogen. The catalyst of this Example I had a surface area (measured by the BET method using nitrogen gas) of about 24.1 sq. meters per gram. The material was allowed to cool, again under nitrogen. The corrosion rate of this catalytic material on Inconel 600 was determined to be about 25 mils per year.

EXAMPLE II

A solution was prepared by dissolving 14.6 g anhydrous $CuCl_2$ and 88.1 g $MgCl_2\ 6H_2O$ in 200 ml water. A second solution was prepared by dissolving 94.1 g KF in 300 ml water. A third solution was prepared by dissolving 6.6 g KCl and 5.4 g LiCl in 100 ml water. The second solution was combined with the first solution. The KF was in excess. A coprecipitate of fluorides was formed according to the equations:

$$CuCl_2 + 2KF \rightarrow CuF_2 + 2KCl$$

$$MgCl_2 + 2KF \rightarrow MgF_2 + 2KCl$$

The slurry was filtered and the filter cake was washed with deionized water. The filter cake, still wet, was reslurried with about 200 ml water. To this slurry was added the third solution and the entire mixture stirred. This mixture was dried and baked for about three days, with occasional hand stirring during the first thick stages. Finally the dried material was calcined for 16 hours at 400° C.

The materials used were in a calculated molar ratio of:

| | |
|---|---|
| $CuCl_2$ | 1.0 M |
| $MgCl_2$ | 4.0 M |
| KCl | 0.82 M |
| LiCl | 1.18 M |

On the basis of theoretical conversion of $CuCl_2$ and $MgCl_2$ to the respective fluorides, the composition of this catalyst on a weight basis is calculated to be:

| | |
|---|---|
| $CuF_2$ | 22.0% |
| $MgF_2$ | 54.0% |
| KCl | 13.2% |

LiCl 10.8%

The catalyst of this Example had a surface area (measured by the BET method using nitrogen gas) of about 8.8 square meters per gram.

EXAMPLE III

The catalyst prepared in Example II was tested in a series of oxychlorofluorination runs with methane and a 50—50 mixture of $CCl_4$ and $CCl_3F$. The results are summarized in the Tables below:

The reactor used consisted essentially of an open ended quartz tube, surrounded by a jacket, and supported in an electrically heated furnace. Reactant gases are supplied through inlet valves and pass out through exit valves. The jacket is sealed to the inner tube near the top of that tube and closes over below the open bottom end of the reactor tube.

The reactant gases enter the jacket through a side arm, flow down the annulus between the jacket and the inner tube to the closed off bottom of the jacket, rise from there into the open end of the reactor tube, pass through the catalyst bed therein, and exit from the top of the reactor tube.

The exit manifold delivers reactants to product separating chromatographic columns and associated detectors, and vent. The flows of the principal reactant gases, HCl, $O_2$, $CH_4$, HF and diluent gas $N_2$ are set and regulated by electronic flow controllers. Total pressure of the combined reactant mixture is recorded by a pressure recorder ahead of the inlet.

Carrier gas helium is controlled by a pressure regulator and diverted to the chromatographic columns.

The initiation, duration and temperature-time profile for a catalyst test run are controlled by a conductive tape programmer, 60-hour clock and percent timer. The tape program, in turn, governs a cam programmer which controls the product gas sampling and analyses. On command from the tape programmer, the cam programmer diverts product gas stream and helium to chromatographic columns. The command also initiates the temperature regimen required for the chromatographic cycle via a Hewlett Packard 5750 chromatographic programmer. Further, the command from the cam diverts the more volatile product gases, not well resolved in the first (high temperature) chromatographic column to the second chromatographic column via a manifold. Finally, the command from the cam initiates the product gas analyzer which furnishes, via thermal conductivity detector bridge circuits, conventional peak trails via the chromatograph peak recorder.

Simultaneously, the bridge circuit emf's are transmitted to two channels of a time-sharing computer and returned as component concentrations via teletype printout. Channel No. 1 printout shows the concentrations of low boiling product components reported in volume percent ($O_2$, $CH_4$, CO), and also gives the reactor temperature, the operating pressure, and a reference flow (usually the HCl flow) all at sampling time. Channel No. 2 printout shows the concentrations of the higher boiling product components: $CO_2$, HCl, $H_2O$, $CH_3Cl$, $COCl_2$, $CH_2Cl_2$, $CHCl_3$, $CCl_4$; as well as for chlorine and HF. A four-point temperature profile from thermocouples along the inside furnace wall is stored continuously by a temperature recorder. The temperature of the sampling valve manifolds is also recorded here.

Inlet concentrations of the reactants are programmed for analysis each hour, during the time while the temperature of the reactor furnace is being changed in a given series of runs over the catalyst.

Table I presents selected data of oxychlorofluorination reactions conducted at various operating conditions using a catalyst composition of the present invention.

TABLE I

| Run No. | Temp. (°C.) | Residence Time (Sec.) | Methane Conversion | Yield | Deacon % | HF Conversion | Selectivity | $CCl_3F$ absolute[a] | $CCl_2F_2$ | Sum of Errors | Performance Factor |
|---|---|---|---|---|---|---|---|---|---|---|---|
| 1 | 500 | 1.57 | 83.6 | 75.4 | 78.4 | 91.0 | 99.6 | 9.31 | 7.29 | 6.4 | 73 |
| 2 | 490 | 1.59 | 77.8 | 76.7 | 75.9 | 91.5 | 99.6 | 9.81 | 7.15 | 10.5 | 70 |
| 3 | 480 | 1.61 | 69.4 | 69.0 | 70.6 | 87.9 | 99.4 | 10.20 | 6.59 | 11.6 | 58 |
| 4 | 470 | 1.64 | 53.3 | 53.0 | 59.0 | 86.1 | 99.5 | 11.55 | 5.77 | 12.2 | 44 |
| 5 | 460 | 1.66 | 39.8 | 39.4 | 51.7 | 82.4 | 99.5 | 12.21 | 5.01 | 9.3 | 35 |
| 6 | 450 | 1.68 | 41.9 | 41.6 | 44.5 | 73.4 | 99.4 | 11.42 | 4.51 | 4.2 | 25 |

[a]Moles per 100 moles of Inlet reactants.

Table II presents the full analytical results of Run No. 1 of Table I.

TABLE II

| Run No. | Residence Time (Sec.) | Temp (°C.) | | $O_2$ | $CH_4$ | $CO_2$ | CO | HCl | HF | $H_2O$ | $CCl_4$ | $CHCl_3$ | $CH_3Cl$ | $CH_2Cl_2$ | $CCl_3F$ | $CHCl_2F$ |
|---|---|---|---|---|---|---|---|---|---|---|---|---|---|---|---|---|
| 1 | 1.57 | 500 | (In) | 24.89 | 11.61 | 0.00 | 0.00 | 31.00 | 18.67 | 0.00 | 6.86 | 0.00 | 0.00 | 0.00 | 6.96 | 0.00 |
| | | | (out)[a] | 7.72 | 1.90 | 0.49 | 0.43 | 17.03 | 1.68 | 32.80 | 2.68 | 2.45 | 0.02 | 0.83 | 9.31 | 0.02 |

[a]Moles per 100 moles of Inlet reactants.

EXAMPLE IV

Another series of runs were conducted using 15.25 grams of the catalytic material prepared in Example II. These runs were conducted in a manner similar to the runs conducted in Example III. Conversions and yields of $CH_4$ and conversions and selectivities of HF were high and the ratio of $CCl_2F_2$ to $CCl_3F$ in the product gases was improved. Pertinent data on these runs are presented in Table III.

TABLE III[a]

| Run Nos. | Res. Time (Sec.) | Temp (°C.) | Inlet[b] | | | | | | CH$_4$ | | Dea-con % | Exit HF | | CCl$_3$F | CCl$_2$F$_2$ | Per-form-ance Factor | Sum of Er-rors |
|---|---|---|---|---|---|---|---|---|---|---|---|---|---|---|---|---|---|
| | | | O$_2$ % | CH$_4$ % | HCl % | HF % | CCl$_4$ % | CCl$_3$F % | Conv. % | Yield % | | Conv. % | Se-lec-tivi-ty % | Absolute[c] | | | |
| 7 | 1.57 | 500 | 24.4 | 10.9 | 30.4 | 20.7 | 6.7 | 6.8 | 99.9 | 88.2 | 85.1 | 100.0 | 99.9 | 6.2 | 10.6 | 94 | 8.3 |
| 8 | 1.61 | 480 | 24.5 | 11.1 | 30.5 | 20.5 | 6.7 | 6.8 | 98.7 | 87.6 | 85.1 | 100.0 | 99.9 | 6.2 | 10.5 | 91 | 7.3 |
| 9 | 1.66 | 460 | 24.9 | 11.5 | 31.1 | 18.7 | 6.9 | 6.9 | 93.8 | 85.0 | 82.8 | 100.0 | 99.7 | 7.2 | 9.2 | 83 | 6.3 |
| 10 | 1.69 | 445 | 24.9 | 11.4 | 31.1 | 18.7 | 6.9 | 6.9 | 89.7 | 81.1 | 79.6 | 96.3 | 99.7 | 7.8 | 8.6 | 76 | 7.2 |

[a]Summary of Runs 1–4 using 15.25 grams of the catalyst having a surface area of 24 square meters per gram and a main pore size of 420 Angstroms.
[b]Reactants flow rates through the reactor was about 131 millimeters per minute.
[c]Moles per 100 moles of Inlet reactants.

In Table IV below, are presented the full analytical results of Runs 7–10 of Table III.

TABLE IV

| Run No. | Residence Time (Sec.) | Temp. (°C.) | O$_2$ | CH$_4$ | CO$_2$ | CO | HCl | HF | H$_2$O | CCl$_4$ | CHCl$_3$ | CH$_3$Cl | CH$_2$Cl$_2$ | CCl$_3$F | CHCl$_2$F | CCl$_2$F$_2$ |
|---|---|---|---|---|---|---|---|---|---|---|---|---|---|---|---|---|
| 7 | 1.57 | 500 (In) | 24.42 | 10.91 | 0.00 | 0.00 | 30.42 | 20.68 | 0.00 | 6.74 | 0.00 | 0.00 | 0.00 | 6.82 | 0.00 | 0.00 |
| | | (Out)[a] | 2.98 | 0.01 | 1.27 | 0.00 | 13.28 | 0.00 | 40.36 | 5.66 | 0.63 | 0.01 | 0.01 | 6.22 | 0.01 | 10.64 |
| 8 | 1.61 | 480 (In) | 24.45 | 11.07 | 0.00 | 0.00 | 30.45 | 20.46 | 0.00 | 6.74 | 0.00 | 0.00 | 0.00 | 6.83 | 0.00 | 0.00 |
| | | (Out) | 3.16 | 0.14 | 1.22 | 0.00 | 13.21 | 0.00 | 40.14 | 5.43 | 1.07 | 0.01 | 0.01 | 6.22 | 0.01 | 10.53 |
| 9 | 1.66 | 460 (In) | 24.93 | 11.47 | 0.00 | 0.00 | 31.05 | 18.70 | 0.00 | 6.88 | 0.00 | 0.00 | 0.00 | 6.97 | 0.00 | 0.00 |
| | | (Out) | 5.35 | 0.71 | 1.00 | 0.00 | 14.58 | 0.00 | 37.16 | 3.90 | 2.67 | 0.01 | 0.59 | 7.19 | 0.01 | 9.23 |
| 10 | 1.69 | 445 (In) | 24.95 | 11.40 | 0.00 | 0.00 | 31.08 | 18.72 | 0.00 | 6.88 | 0.00 | 0.00 | 0.00 | 6.97 | 0.00 | 0.00 |
| | | (Out) | 6.82 | 1.18 | 0.95 | 0.00 | 16.62 | 0.70 | 34.37 | 3.12 | 2.69 | 0.01 | 0.94 | 7.75 | 0.01 | 8.59 |

[a]Moles per 100 moles of Inlet reactants.

What is claimed is:

1. A novel catalyst composition which comprises in combination at least about 60% by weight of said composition of magnesium and copper ions, each in combination with fluoride ion and at least one alkali metal in combination with chloride ion.

2. The catalyst of claim 1 wherein the alkali metal is selected from the group consisting of at least one of sodium, lithium, potassium, rubidium and cesium.

3. The catalyst of claim 1 wherein the alkali metal is sodium.

4. The catalyst of claim 1 wherein the alkali metal is potassium.

5. The catalyst of claim 1 wherein the alkali metal is lithium.

6. The catalyst of claim 1 wherein the alkali metal is a mixture of potassium and lithium.

7. The catalyst of claim 1 comprising a mixture of magnesium fluoride, copper fluoride, potassium chloride and lithium chloride.

8. The catalyst of claim 1 which has been prepared by coprecipitating magnesium fluoride and copper fluoride from an aqueous solution of salts thereof and then incorporating a source of the alkali metal.

9. The catalyst of claim 8 which has been filtered prior to incorporation of the alkali metal and, after incorporation, heated at about 400°–700° C. and then washed with an organic solvent.

* * * * *